US011382849B2

(12) United States Patent
Ronchard et al.

(10) Patent No.: US 11,382,849 B2
(45) Date of Patent: *Jul. 12, 2022

(54) NON-DYEING COMPOSITION COMPRISING A CATIONIC ACRYLIC COPOLYMER AND A CONDITIONING AGENT

(71) Applicant: L'Oreal, Paris (FR)

(72) Inventors: Guillaume Ronchard, Saint-Chamond (FR); Stéphanie Coulombel, Saint-Ouen (FR)

(73) Assignee: L'OREAL, Paris (FR)

( * ) Notice: Subject to any disclaimer, the term of this patent is extended or adjusted under 35 U.S.C. 154(b) by 679 days.

This patent is subject to a terminal disclaimer.

(21) Appl. No.: 16/063,799

(22) PCT Filed: Dec. 22, 2016

(86) PCT No.: PCT/EP2016/082504
§ 371 (c)(1),
(2) Date: Jun. 19, 2018

(87) PCT Pub. No.: WO2017/109147
PCT Pub. Date: Jun. 29, 2017

(65) Prior Publication Data
US 2020/0261338 A1    Aug. 20, 2020

(30) Foreign Application Priority Data

Dec. 22, 2015    (FR) ...................................... 1563081

(51) Int. Cl.
*A61Q 5/06*    (2006.01)
*A61K 8/41*    (2006.01)
*A61K 8/81*    (2006.01)
*A61K 8/898*    (2006.01)

(52) U.S. Cl.
CPC ............ *A61K 8/416* (2013.01); *A61K 8/8152* (2013.01); *A61K 8/898* (2013.01); *A61Q 5/06* (2013.01); *A61K 2800/10* (2013.01); *A61K 2800/42* (2013.01); *A61K 2800/5426* (2013.01)

(58) Field of Classification Search
None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Sock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,157,388 A | 6/1979 | Christiansen |
| 4,165,367 A | 8/1979 | Chakrabarti |
| 4,172,887 A | 10/1979 | Vanlerberghe et al. |
| 4,185,087 A | 1/1980 | Morlino |

(Continued)

FOREIGN PATENT DOCUMENTS

| | | |
|---|---|---|
| EP | 0080976 A1 | 6/1983 |
| EP | 0122324 A1 | 10/1984 |

(Continued)

OTHER PUBLICATIONS

Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Anonymous: "Silsoft * A +, conditioning agent," Dec. 1, 2009, XP055294140, Retrieved from the Internet: http://s3.amazonaws.com/zanran_storage/www.momentive.com/ContentPages/45675670.pdf [retrieved on Aug. 8, 2016].
Floyd et al., "Performance-Driven: New Silicone CoPolymers—Experimenting with Dimethicone Copolyols for personal-care products," GCI, Global Cosmetic Industry, vol. 167, No. 3, Sep. 1, 2000, p. 26.

(Continued)

*Primary Examiner* — Jyothsna A Venkat
(74) *Attorney, Agent, or Firm* — The Marbury Law Group, PLLC

(57) ABSTRACT

The present invention relates to a non-dyeing composition comprising: (i) one or more cationic acrylic copolymers comprising at least the units obtained from the following monomers: a) monomer derived from acrylic or methacrylic esters or amides and comprising at least one cationic group, and b) alkyl acrylate or methacrylate monomer, the alkyl radical comprising from 1 to 30 carbon atoms, preferably 1 to 22 carbon atoms, better still 1 to 10 carbon atoms and preferentially 2 to 6 carbon atoms. and (ii) one or more conditioning agents chosen from functionalized silicones, cationic polymers and cationic surfactants, and mixtures thereof.

17 Claims, No Drawings

(56) References Cited

U.S. PATENT DOCUMENTS

| | | |
|---|---|---|
| 4,197,865 A | 4/1980 | Jacquet et al. |
| 4,217,914 A | 8/1980 | Jacquet et al. |
| 4,240,450 A | 12/1980 | Grollier et al. |
| 4,349,532 A | 9/1982 | Vanlerberghe et al. |
| 4,591,610 A | 5/1986 | Grollier |
| 4,702,906 A | 10/1987 | Jacquet et al. |
| 4,719,282 A | 1/1988 | Nadolsky et al. |
| 4,761,273 A | 8/1988 | Grollier et al. |
| 4,839,166 A | 6/1989 | Grollier et al. |
| 4,874,554 A | 10/1989 | Lange et al. |
| 4,996,059 A | 2/1991 | Grollier et al. |
| 5,089,252 A | 2/1992 | Grollier et al. |
| 2016/0206547 A1* | 7/2016 | Alves ............... A61K 8/31 |

FOREIGN PATENT DOCUMENTS

| | | | |
|---|---|---|---|
| EP | 0337354 A1 | 10/1989 | |
| EP | 0530974 A1 | 3/1993 | |
| EP | 2883533 A1 * | 6/2015 | ............... A61Q 5/12 |
| FR | 1492597 A | 8/1967 | |
| FR | 1583363 A | 10/1969 | |
| FR | 2077143 A5 | 10/1971 | |
| FR | 2080759 A1 | 11/1971 | |
| FR | 2162025 A | 7/1973 | |
| FR | 2190406 A2 | 2/1974 | |
| FR | 2252840 A1 | 6/1975 | |
| FR | 2270846 A1 | 12/1975 | |
| FR | 2280361 A2 | 2/1976 | |
| FR | 2316271 A1 | 1/1977 | |
| FR | 2320330 A1 | 3/1977 | |
| FR | 2336434 A1 | 7/1977 | |
| FR | 2368508 A2 | 5/1978 | |
| FR | 2383660 A1 | 10/1978 | |
| FR | 2393573 A1 | 1/1979 | |
| FR | 2413907 A1 | 8/1979 | |
| FR | 2470596 A1 | 6/1981 | |
| FR | 2505348 A1 | 11/1982 | |
| FR | 2519863 A1 | 7/1983 | |
| FR | 2542997 A1 | 9/1984 | |
| FR | 2598611 A1 | 11/1987 | |
| GB | 1546809 A | 5/1979 | |
| JP | 3414493 B2 | 6/2003 | |
| JP | 5745266 B2 | 7/2015 | |
| WO | 03011969 A1 | 2/2003 | |

OTHER PUBLICATIONS

GOO Chemical: "Personal Care Product Catalogue for Cosmetics," Internet Citation, Jan. 2015, pp. 1-12, XP002759716, Retrieved from the Internet: http://www.goo-chem.co.jp/english/product/pdf/cosmetic/cosmetics_catalogue_en_2013.pdf [retrieved on Jul. 11, 2016].

Ruetsch et al. "The Role of Cationic Conditioning Compounds in Reinforcement of the Cuticula," Journal of Cosmetic Science, XP055294540, Jan. 1, 2003, pp. 63-83. Retrieved from the Internet: http://journal.scconline.org/pdf/cc2003/cc054n01/p00063-p00083.pdf.

International Search Report for Application No. PCT/EP2016/082504, dated Feb. 15, 2017.

* cited by examiner

NON-DYEING COMPOSITION COMPRISING A CATIONIC ACRYLIC COPOLYMER AND A CONDITIONING AGENT

CROSS REFERENCE TO RELATED APPLICATIONS

This is a national stage application of PCT/EP2016/082504, filed internationally on Dec. 22, 2016, which claims priority to French Application No. 1563081 filed on Dec. 22, 2015, both of which are incorporated by reference herein in their entireties.

The present invention relates to a non-dyeing composition, especially a cosmetic composition, comprising one or more particular cationic acrylic copolymers and one or more particular conditioning agents.

The invention also relates to a cosmetic process for treating keratin fibres using this composition.

The invention finally relates to the use of such a composition in the cosmetic treatment of keratin fibres and in particular the hair.

Many non-invasive technologies now exist for satisfying styling needs. Styling products are usually used to construct and structure the hairstyle and to give it long-lasting hold. These compositions generally comprise one or more fixing film-forming polymers, in a cosmetically acceptable medium. These polymers allow the formation of a coating film on the hair, or the formation of micro-welds between the individual hairs, thus ensuring the hairstyle hold.

Styling products are generally in the form of lacquers, mousses or gels. In particular, styling gels are often used in order to obtain strong fixing of the hairstyle. Styling gels are solutions of one or more fixing film-forming polymers, thickened or gelled with one or more thickening polymers.

However, the effects provided by these technologies disappear during the first shampoo wash and it is necessary to reapply them in order to obtain the desired effect. This imposes a more or less long and tedious routine on the consumer. For example, for a blow-drying product for frizzy hair, after applying the styling spray, the product needs to be distributed uniformly over the entire head of hair followed by performing blow-drying, which may take from 5 to 45 minutes depending on the desired result.

In contrast, long-lasting shape products allow the structure of the fibre to be definitively modified by breaking (reducing) the disulfide bonds which impose the original shape of the hair, followed by re-bridging (e.g.: oxidation of the cysteines to cystine after a mechanical action such as the insertion of curlers in the case of permanent waving). These products must, however, be reapplied at the root once hair regrowth occurs in order to conserve a uniform result. The results are irreversible and sensitize the hair. The superposition of relaxing products, for example, may cause discomfort and, in the long-term, lead to real degradation of the fibre which may be up to the point of breakage.

The object of a semi-permanent styling product is to offer satisfaction as regards the durability of the styling effects after one or more shampoo washes, while at the same time preserving the integrity of the fibre so as to offer the consumer timesaving and improved safety. The term "styling effect" means performance in terms of manageability, provision of body, curl definition, volume control, sheen, ease of shaping by natural drying, blow-drying and/or drying using flat tongs, and hairsetting. Ideally, it is also expected of this type of product that it be readily removable by means of an action or by a composition acting as a makeup remover.

Furthermore, the product must not generate static electricity.

There is thus a need to formulate a composition, especially a composition which gives the treated fibre coating of the fibre, which satisfies the following criteria:
  being adherent to the fibre and remaining perceptible after several shampoo washes,
  allowing the hair to be easily and durably shaped,
  affording good cosmetic qualities,
  being simple to use, without any risk of damaging the hair,
  being compatible with the hair treatments conventionally used (shampooing, hair conditioning, dyeing), but also with sebum.

It has now been discovered that a combination of one or more particular cationic acrylic polymers and one or more particular conditioning agents makes it possible to generate coating around the fibre which affords the desired styling properties, while at the same time being friendly to the fibre. What is more, this coating is persistent with respect to shampooing. Furthermore, this composition has good working qualities (distribution, disentangling of dry and wet hair, individualization).

One subject of the invention is thus especially a non-dyeing composition comprising:
  (i) one or more cationic acrylic copolymers comprising at least the units obtained from the following monomers:
    a) monomer derived from acrylic or methacrylic esters or amides and comprising at least one cationic or cationizable group, and
    b) alkyl acrylate or methacrylate monomer, and
  (ii) one or more conditioning agents chosen from functionalized silicones, cationic polymers and cationic surfactants, and mixtures thereof.

The composition according to the invention is preferably a composition for treating keratin fibres, in particular human keratin fibres such as the hair.

A subject of the present invention is also a cosmetic process for treating keratin fibres, in particular human keratin fibres such as the hair, in which the composition according to the invention is applied to said fibres.

Another subject of the invention is the use of said composition for the cosmetic treatment of keratin fibres, in particular human keratin fibres such as the hair.

It was observed that the fibres thus treated have coating that is persistent with respect to shampooing. The composition thus applied gives shaping properties that have good working qualities (distribution, disentangling of dry and wet hair, individualization) on application and after shampooing.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

According to the present application, "keratin fibres" means human keratin fibres and more specifically hair.

For the purposes of the present invention, the term "non-dyeing composition" means a composition which does not comprise any direct dye or oxidation dye precursor (oxidation base and coupler) or any other compound which, by reaction, gives a coloured species in the composition or on the fibres, usually used for dyeing human keratin fibres, or alternatively, if it does comprise any, the total amount thereof does not exceed 0.005% by weight relative to the weight of the composition. Specifically, at such a content, only the composition would be dyed, i.e. no dyeing effect would be observed on the keratin fibres.

It is recalled that oxidation dye precursors, oxidation bases and couplers are colourless or sparingly coloured compounds, which, via a condensation reaction in the presence of an oxidizing agent, give a coloured species. With regard to direct dyes, these compounds are coloured and have a certain affinity for keratin fibres.

Copolymer

The non-dyeing composition according to the invention comprises at least one acrylic cationic copolymer, comprising at least the units obtained from the following monomers:

a) monomer derived from acrylic or methacrylic esters or amides and comprising at least one cationic group, and b) alkyl acrylate or methacrylate monomer, the alkyl radical comprising from 1 to 30 carbon atoms, preferably 1 to 22 carbon atoms, better still 1 to 10 carbon atoms and preferentially 2 to 6 carbon atoms.

For the purposes of the present invention, the term "cationic compound or group" means a compound or group bearing a permanent cationic charge or a charge obtained by protonation of a (cationizable) function, such as an amine function, by the protons of the medium.

Preferably, the copolymer according to the invention is water-insoluble. For the purposes of the present invention, the term "water-insoluble" refers to a compound that is insoluble in water at ordinary temperature (25° C.) and at atmospheric pressure (760 mmHg or $1.013 \times 10^5$ Pa) (solubility of less than 5%, preferably 1% and even more preferentially 0.1%).

Preferentially, the acrylic cationic copolymer contains c) at least a third unit obtained from a polymerizable ethylenic monomer, preferably from a monomer having the following formula:

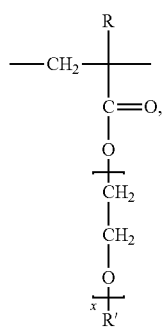

(A')

in which R and R', which may be identical or different, represent a hydrogen atom, a C1-C10 and preferably C1-C4 alkyl radical; preferably, R is a methyl radical; better still, R is a methyl radical and R' is an ethyl radical;

x ranging from 1 to 10, preferably from 1 to 3, and better still x is 1.

More particularly, the acrylic cationic copolymer present in the composition according to the invention comprises at least units obtained from the following two lists of monomers:

a) monomer derived from acrylic or methacrylic esters or amides and comprising at least one cationic group, having the following formulae:

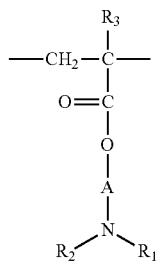

(I)

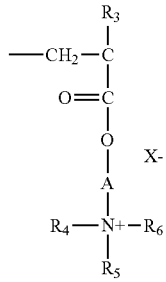

(II)

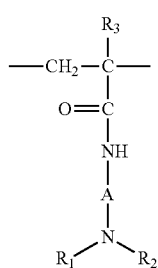

(III)

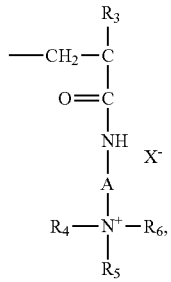

(IV)

in which:

$R_3$, which may be identical or different, denote a hydrogen atom or a $CH_3$ group;

A, which may be identical or different, represent a linear or branched divalent alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl group, and preferably an alkyl group containing from 1 to 6 carbon atoms;

$R_1$ and $R_2$, which may be identical or different, represent a hydrogen atom or an alkyl group containing from 1 to 6 carbon atoms, and preferably methyl or ethyl;

X denotes an anion derived from a mineral or organic acid, such as a methosulfate anion or a halide such as chloride or bromide.

b) $C_1$-$C_{30}$, preferably $C_1$-$C_{22}$, preferentially $C_1$-$C_{10}$ and better still $C_2$-$C_6$ alkyl acrylate or methacrylate monomer.

Even more preferentially, the acrylic cationic copolymer present in the composition according to the invention comprises at least the units obtained from the following monomers:

a) monomer derived from acrylic or methacrylic esters or amides and comprising at least one cationic group, having the following formulae:

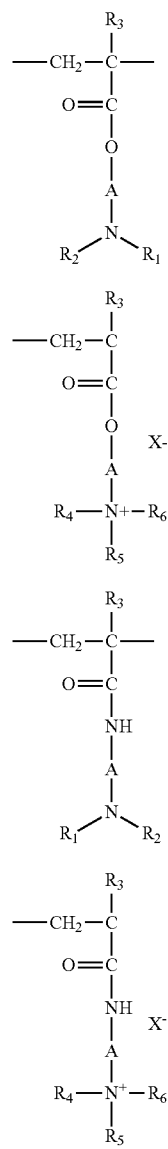

in which:

$R_3$, which may be identical or different, denote a hydrogen atom or a $CH_3$ group;

A, which may be identical or different, represent a linear or branched divalent alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl group, and preferably an alkyl group containing from 1 to 6 carbon atoms;

$R_1$ and $R_2$, which may be identical or different, represent a hydrogen atom or an alkyl group containing from 1 to 6 carbon atoms, and preferably methyl or ethyl;

X denotes an anion derived from a mineral or organic acid, such as a methosulfate anion or a halide such as chloride or bromide, preferably, formulae (I) and (II)

b) $C_1$-$C_{30}$, preferably $C_1$-$C_{22}$, preferentially $C_1$-$C_{10}$ and better still $C_2$-$C_6$ alkyl acrylate or methacrylate monomer, and c) at least a third unit obtained from a polymerizable ethylenic monomer, preferably from a monomer having the following formula:

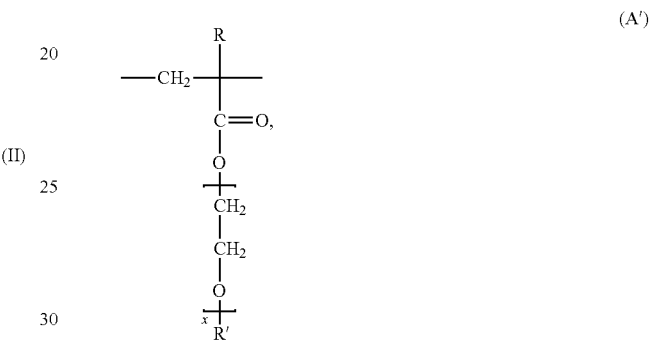

in which R and R', which may be identical or different, represent a hydrogen atom, a $C_1$-$C_{10}$ and preferably $C_1$-$C_4$ alkyl radical; preferably, R is a methyl radical; better still, R is a methyl radical and R' is an ethyl radical;

x ranging from 1 to 10, preferably from 1 to 3, and better still x is 1.

Even more particularly, the composition according to the invention comprises at least one copolymer comprising at least the units obtained from the following monomers:

a) a monomer derived from acrylic or methacrylic esters of formula (I) or (II) as described previously, preferably of formula (II), b) a $C_1$-$C_{22}$, preferably $C_1$-$C_{10}$ and better still $C_2$-$C_6$ alkyl acrylate or methacrylate monomer, c) a monomer of formula (A') as described previously.

Most particularly, the composition comprises one or more cationic acrylic copolymers, which are preferably water-insoluble, bearing the following units:

a) methacryloyloxyethyltrimethylammonium salt,
b) butyl methacrylate, and
c) ethoxyethyl methacrylate.

Such copolymers are described, for example, in JP5745266. Preferably, the polymer contains the preceding three monomers in the following proportions relative to the total number of monomer units, by weight in the constituted copolymer, without taking into account the salts thereof:

a) in a proportion of 0.5% to 20%, preferably between 1% and 5%;

b) in a proportion of 20% to 98%, preferably between 40% and 97%;

c) in a proportion of 1.5% to 95%, preferably between 2% and 55%.

Preferably, the copolymer is not amphoteric, i.e. it does not comprise any units bearing an anionic charge.

Preferably, the units of the copolymer are all methacrylate derivatives.

Even more particularly, the copolymer corresponds to the copolymer whose INCI name is Polyquaternium-99, for instance the polymer sold by the company GOO-Chemical under the name Plascize L-514.

It is the butyl methacrylate/ethoxyethyl methacrylate/methacryloyloxyethyltrimethylammonium chloride copolymer, at 30% in ethanol:

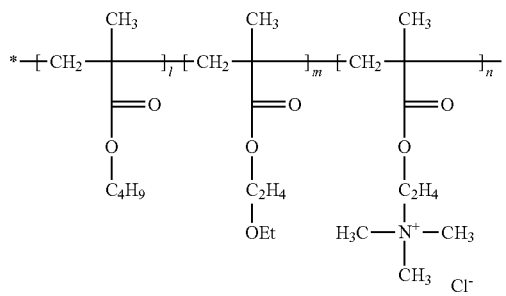

The content of copolymer in the composition according to the invention may range from 0.05% to 15% by weight relative to the total weight of the composition, preferably from 0.1% to 10% by weight and more preferentially from 1% to 7% by weight relative to the total weight of the composition.

Conditioning Agents

The composition according to the invention comprises one or more conditioning agents chosen from functionalized silicones, cationic polymers and cationic surfactants, and a mixture thereof.

Functionalized Silicones

Preferably, the conditioning agent is an organomodified polysiloxane comprising at least one functional group preferably chosen from amine groups, alkoxy groups, hydroxyl groups and reactive groups.

Organopolysiloxanes are defined in greater detail in Walter Noll's *Chemistry and Technology of Silicones* (1968), Academic Press.

The organomodified silicones that may be used in accordance with the invention are silicones comprising in their structure one or more organofunctional groups as mentioned previously, attached via a hydrocarbon-based group.

The conditioning agent may be one or more amino silicones. The term "amino silicone" denotes any silicone comprising at least one primary, secondary or tertiary amine or a quaternary ammonium group.

The weight-average molecular masses of these amino silicones may be measured by gel permeation chromatography (GPC) at room temperature (25° C.), as polystyrene equivalent. The columns used are μ styragel columns. The eluent is THF and the flow rate is 1 ml/min. 200 μl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

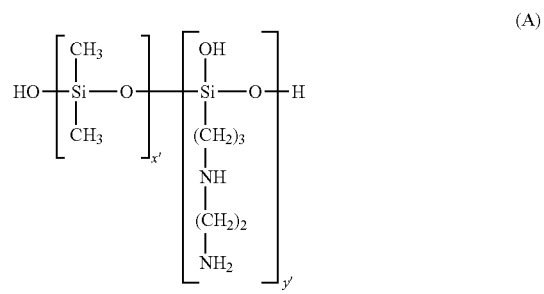

in which x' and y' are integers such that the weight-average molecular weight (Mw) is between 5000 and 500 000 approximately;

b) the amino silicones corresponding to formula (B):

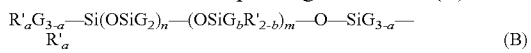

in which:

G, which may be identical or different, denotes a hydrogen atom or a phenyl, OH or $C_1$-$C_8$ alkyl group, for example methyl, or a $C_1$-$C_8$ alkoxy group, for example methoxy, a, which may be identical or different, denotes 0 or an integer from 1 to 3, in particular 0, b denotes 0 or 1, in particular 1, m and n are numbers such that the sum (n+m) ranges from 1 to 2000 and in particular from 50 to 150, n possibly denoting a number from 0 to 1999 and especially from 49 to 149, and m possibly denoting a number from 1 to 2000 and especially from 1 to 10;

R', which may be identical or different, denotes a monovalent radical of formula —$C_qH_{2q}L$ in which q is a number ranging from 2 to 8 and L is an optionally quaternized amino group chosen from the following groups:

—N(R")$_2$; —N$^+$(R")$_3$A-; —NR"-Q-N(R")$_2$ and —NR"-Q-N$^+$(R")$_3$A-, in which R", which may be identical or different, denotes hydrogen, phenyl, benzyl, or a saturated monovalent hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and A- represents a cosmetically acceptable anion, especially a halide such as fluoride, chloride, bromide or iodide.

Preferably, the amino silicones are chosen from the amino silicones of formula (B).

Preferably, the amino silicones of formula (B) are chosen from the amino silicones corresponding to formulae (C), (D), (E), (F) and/or (G) below.

According to a first embodiment, the amino silicones corresponding to formula (B) are chosen from the silicones known as "trimethylsilyl amodimethicone" corresponding to formula (C):

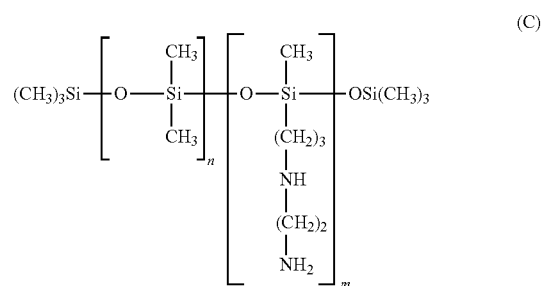

in which m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10.

According to a second embodiment, the amino silicones corresponding to formula (B) are chosen from the silicones of formula (D) below:

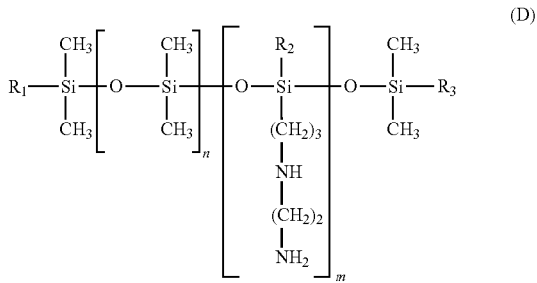

(D)

in which:

m and n are numbers such that the sum (n+m) ranges from 1 to 1000 and in particular from 50 to 250 and more particularly from 100 to 200; it being possible for n to denote a number from 0 to 999 and in particular from 49 to 249 and more particularly from 125 to 175, and for m to denote a number from 1 to 1000 and in particular from 1 to 10, and more particularly from 1 to 5;

R1, R2 and R3, which may be identical or different, represent a hydroxyl or C1-C4 alkoxy radical, at least one of the radicals R1 to R3 denoting an alkoxy radical.

Preferably, the alkoxy radical is a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular mass (Mw) of these silicones preferably ranges from 2000 to 1 000 000 and more particularly from 3500 to 200 000.

According to a third embodiment, the amino silicones corresponding to formula (B) are chosen from the silicones of formula (E) below:

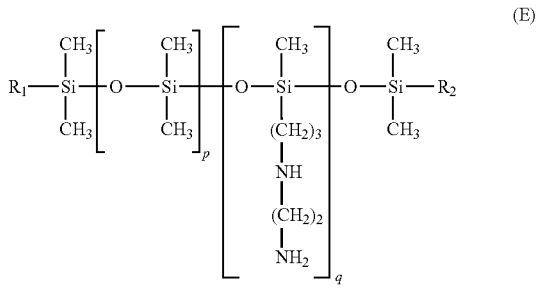

(E)

in which:

p and q are numbers such that the sum (p+q) ranges from 1 to 1000, in particular from 50 to 350 and more particularly from 150 to 250; it being possible for p to denote a number from 0 to 999 and especially from 49 to 349 and more particularly from 159 to 239, and for q to denote a number from 1 to 1000, especially from 1 to 10 and more particularly from 1 to 5;

R1 and R2, which are different, represent a hydroxyl or C1-C4 alkoxy radical, at least one of the radicals R1 or R2 denoting an alkoxy radical.

Preferably, the alkoxy radical is a methoxy radical.

The hydroxy/alkoxy mole ratio generally ranges from 1:0.8 to 1:1.1, preferably from 1:0.9 to 1:1 and is more particularly equal to 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones whose structure is different from formula (D) or (E).

A product containing amino silicones of structure (D) is sold by the company Wacker under the name Belsil® ADM 652.

A product containing amino silicones of structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic.

The numerical mean size of the silicone particles in the emulsion generally ranges from 3 nm to 500 nm. Preferably, especially as amino silicones of formula (E), use is made of microemulsions whose mean particle size ranges from 5 nm to 60 nm (limits inclusive) and more particularly from 10 nm to 50 nm (limits inclusive). Thus, use may be made according to the invention of the amino silicone microemulsions of formula (E) sold under the names Finish CT 96 E® or SLM 28020® by the company Wacker.

According to a fourth embodiment, the amino silicones corresponding to formula (B) are chosen from the silicones of formula (F) below:

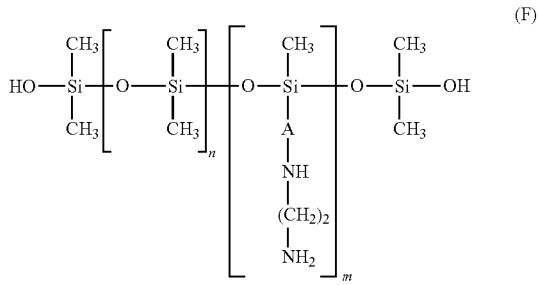

(F)

in which:

m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;

A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1 000 000 and even more particularly from 3500 to 200 000.

An emulsion corresponding to this formula is, for example, Xiameter MEM 8299 Emulsion from Dow Corning.

According to a fifth embodiment, the amino silicones corresponding to formula (B) are chosen from the silicones of formula (G) below:

$$\text{(G)}$$

$$H_3C-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n\left[\underset{\underset{\underset{NH_2}{|}}{\underset{(CH_2)_2}{|}}}{\overset{\overset{CH_3}{|}}{Si}}-O\right]_m-\underset{\underset{CH_3}{|}}{\overset{\overset{CH_3}{|}}{Si}}-CH_3$$

in which:

m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;

A denotes a linear or branched alkylene radical containing from 4 to 8 carbon atoms and preferably 4 carbon atoms. This radical is preferably branched.

The weight-average molecular mass (Mw) of these amino silicones preferably ranges from 500 to 1 000 000 and even more particularly from 1000 to 200 000.

A silicone corresponding to this formula is, for example, DC2-8566 Amino Fluid from Dow Corning.

c) the amino silicones corresponding to formula (H):

$$\text{(H)}$$

$$(R_5)_3-Si-O\left[\underset{\underset{R_5}{|}}{\overset{\overset{R_5}{|}}{Si}}-O\right]_r\left[\underset{\underset{R_5}{|}}{\overset{\overset{R_6-CH_2-CHOH-CH_2-N^+(R_5)_3}{|}}{Si}}-O\right]_s-Si-(R_5)_3 \quad Q^-$$

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

Q- is an anion such as a halide ion, especially chloride, or an organic acid salt, especially acetate;

r represents a mean statistical value from 2 to 20 and in particular from 2 to 8;

s represents a mean statistical value from 20 to 200 and in particular from 20 to 50.

Such amino silicones are especially described in patent U.S. Pat. No. 4,185,087;

d) the quaternary ammonium silicones of formula (I):

$$\text{(I)}$$

$$R_8-\underset{\underset{R_7}{|}}{\overset{\overset{R_7}{|}}{N^+}}-CH_2-\underset{\overset{OH}{|}}{CH}-CH_2-R_6\left[\underset{\underset{R_7}{|}}{\overset{\overset{R_7}{|}}{Si}}-O\right]_r\underset{\underset{R_7}{|}}{\overset{\overset{R_7}{|}}{Si}}-R_6-CH_2-CHOH-CH_2-\underset{\underset{R_7}{|}}{\overset{\overset{R_7}{|}}{N^+}}-R_8 \quad 2X^-$$

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—NHCOR$_7$;

X- is an anion such as a halide ion, especially chloride, or an organic acid salt, especially acetate;

r represents a mean statistical value ranging from 2 to 200 and in particular from 5 to 100.

These silicones are described, for example, in patent application EP-A 0 530 974.

e) the amino silicones of formula (J):

$$\text{(J)}$$

$$H_2N-(C_mH_{2m})-NH-(C_nH_{2n})-Si\left[O\left[\underset{\underset{R_2}{|}}{\overset{\overset{R_1}{|}}{Si}}-O\right]_x\underset{\underset{R_4}{|}}{\overset{\overset{R_3}{|}}{Si}}-R_5\right]_3$$

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and x is chosen such that the amine number ranges from 0.01 to 1 meq/g;

f) the multiblock polyoxyalkylenated amino silicones, of the type (AB)n, A being a polysiloxane block and B being a polyoxyalkylene block comprising at least one amine group. Said silicones preferably are constituted of repeating units of the following general formulae:

[—(SiMe$_2$O)$_x$SiMe$_2$—R—N(R")—R'—O(C$_2$H$_4$O)$_a$
(C$_3$H$_6$O)$_b$—R'—N(H)—R—]

or alternatively

[—(SiMe$_2$O)$_x$SiMe$_2$—R—N(R")—R'—O(C$_2$H$_4$O)$_a$
(C$_3$H$_6$O)$_b$—]

in which:

a is an integer greater than or equal to 1, preferably ranging from 5 to 200 and more particularly ranging from 10 to 100;

b is an integer between 0 and 200, preferably ranging from 4 to 100 and more particularly between 5 and 30;

x is an integer ranging from 1 to 10 000 and more particularly from 10 to 5000;

R″ is a hydrogen atom or a methyl;

R, which may be identical or different, represent a divalent linear or branched C2-C12 hydrocarbon-based radical, optionally including one or more heteroatoms such as oxygen; preferably, R denotes an ethylene radical, a linear or branched propylene radical, a linear or branched butylene radical, or a —CH2CH2CH2OCH(OH)CH2— radical; preferentially R denotes a —CH2CH2CH2OCH(OH)CH2— radical;

R', which may be identical or different, represent a linear or branched C2-C12 divalent hydrocarbon-based radical, optionally comprising one or more heteroatoms such as oxygen; preferably, R' denotes an ethylene radical, a linear or branched propylene radical, a linear or branched butylene radical, or a —CH2CH2CH2OCH(OH)CH2— radical; preferentially, R denotes —CH(CH3)—CH2—.

The siloxane blocks preferably represent between 50 mol % and 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may be made especially of the silicones sold under the names Silsoft A-843 or Silsoft A+ by Momentive.

g) and mixtures thereof.

Preferably, the amino silicones are chosen from multiblock polyoxyalkylenated amino silicones.

The conditioning agent may be an alkoxy silicone, such as the product sold under the name Silicone Copolymer F-755 by SWS Silicones, and Abil Wax® 2428, 2434 and 2440 by the company Goldschmidt.

The conditioning agent may be a silicone bearing hydroxyl group(s), for instance alpha,omega-dihydroxy-terminated polydimethylsiloxanes, such as the compounds having the INCI name dimethiconol, alone or in emulsion or as a mixture, including the dimethicone/dimethiconol mixture sold under the name Xiameter PMX-1503 Fluid by Dow Corning or the dimethiconol/dimethicone/isohexadecane and isoparaffin mixture sold under the name Xiameter PMX-1503 Fluid by Dow Corning.

The composition according to the invention may comprise the functionalized silicone(s), preferably amino silicone(s), in an amount ranging from 0.01% to 15% by weight, preferably from 0.05% to 10% by weight and preferentially from 0.1% to 5% by weight, relative to the total weight of the composition.

The composition may also comprise one or more cationic polymers other than the cationic acrylic copolymers as described previously.

For the purposes of the present invention, the term "cationic polymer" denotes any polymer containing cationic groups and/or groups that can be ionized into cationic groups.

The cationic polymers that may be present in the composition according to the invention may be chosen from any of those already known per se as improving the cosmetic properties of the hair, i.e. especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or be carried by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers, mention may more particularly be made of polymers of the type such as polyamine, polyaminoamide and polyquaternary ammonium.

These are known products. They are especially described in French patents no 2 505 348 and 2 542 997. Among said polymers, mention may be made of:

(1) Homopolymers or copolymers derived from acrylic or methacrylic esters or amides and comprising at least one of the units of formula (IX), (X), (XI) or (XII) below, other than the cationic acrylic copolymers as described previously:

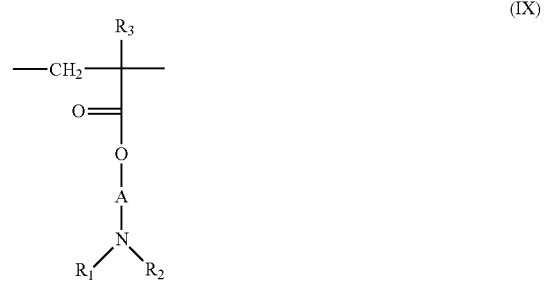

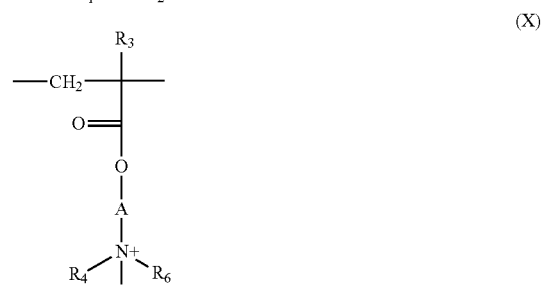

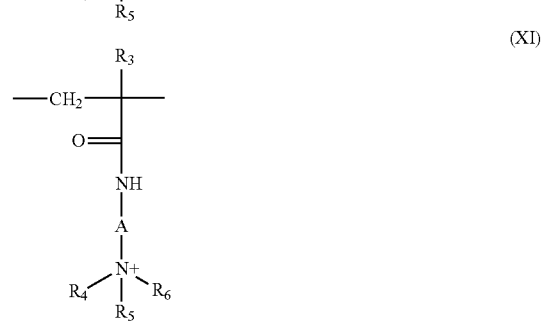

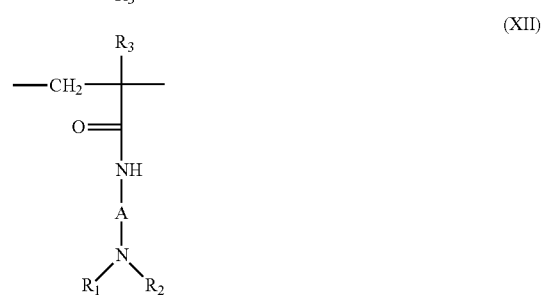

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

X denotes an anion derived from a mineral or organic acid, such as a methosulfate anion or a halide such as chloride or bromide.

Mention may be made in particular of the ethyltrimethylammonium methacrylate chloride homopolymer.

The polymers of family (1) may also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. Use may more particularly be made of a crosslinked acrylamide/methacryloyloxyethyltrimethylammonium chloride copolymer (20/80 by weight) in the form of a dispersion containing 50% by weight of said copolymer in mineral oil. This dispersion is sold under the name Salcare® SC 92 by the company Ciba. Use may also be made of a crosslinked homopolymer of methacryloyloxyethyltrimethylammonium chloride containing approximately 50% by weight of the homopolymer in mineral oil or in a liquid ester. These dispersions are sold under the names Salcare® SC 95 and Salcare® SC 96 by the company Ciba.

(2) Cellulose ether derivatives containing quaternary ammonium groups, described in French patent 1 492 597, and in particular polymers sold under the names Ucare Polymer JR (JR 400 LT, JR 125 and JR 30M) or LR (LR 400 or LR 30M) by the company Amerchol. These polymers are also defined in the CTFA dictionary as quaternary ammoniums of hydroxyethylcellulose that have reacted with an epoxide substituted with a trimethylammonium group.

(3) Cellulose copolymers or cellulose derivatives grafted with a water-soluble monomer of quaternary ammonium, and described especially in U.S. Pat. No. 4,131,576, such as hydroxyalkylcelluloses, for instance hydroxymethyl-, hydroxyethyl- or hydroxypropyl-celluloses grafted, in particular, with a methacryloylethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch.

(4) The cationic guar gums described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 or Jaguar C162 by the company Rhodia.

(5) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are especially described in French patents 2 252 840 and 2 368 508.

(7) Polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Such polymers are in particular described in French patent 1 583 363.

Among these derivatives, mention may be made more particularly of the adipic acid/dimethylamino-hydroxy-propyl/diethylenetriamine polymers sold under the name Cartaretine F, F4 or F8 by the company Sandoz.

(8) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The mole ratio between the polyalkylene polyamine and the dicarboxylic acid is between 0.8:1 and 1.4:1; the polyaminoamide resulting therefrom is reacted with epichlorohydrin in a mole ratio of epichlorohydrin relative to the secondary amine group of the polyaminoamide of between 0.5:1 and 1.8:1. Such polymers are described in particular in U.S. Pat. Nos. 3,227,615 and 2,961,347.

Polymers of this type are sold in particular under the name Hercosett 57 by Hercules Inc. or else under the name PD 170 or Delsette 101 by Hercules in the case of the adipic acid/epoxypropyl/diethylenetriamine copolymer.

(9) Cyclopolymers of alkyldiallylamine or of dialkyldiallylammonium, such as homopolymers or copolymers comprising, as main constituent of the chain, units corresponding to formula (XIII) or (XIV):

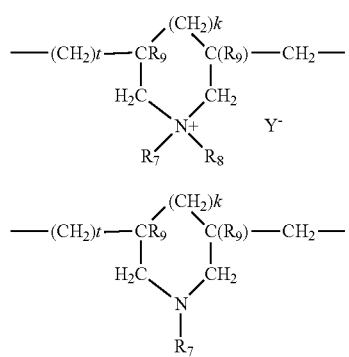

in which formulae k and t are equal to 0 or 1, the sum k+t being equal to 1; $R_9$ denotes a hydrogen atom or a methyl radical; $R_7$ and $R_8$, independently of each other, denote an alkyl group containing from 1 to 6 carbon atoms, a hydroxyalkyl group in which the alkyl group preferably contains 1 to 5 carbon atoms, or a lower ($C_1$-$C_4$) amidoalkyl group, or $R_7$ and $R_8$ may denote, together with the nitrogen atom to which they are attached, heterocyclic groups, such as piperidyl or morpholinyl; $R_7$ and $R_8$, independently of each other, preferably denote an alkyl group containing from 1 to 4 carbon atoms; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

Among the polymers defined above, mention may be made more particularly of the dimethyldiallylammonium chloride homopolymer sold under the name Merquat 100 by the company Nalco (and its homologues of low weight-average molecular mass) and the copolymers of diallyldimethylammonium chloride and of acrylamide, sold under the names Merquat 550 and Merquat 7SPR.

(10) The quaternary diammonium polymer containing repeating units corresponding to formula (XV):

in which formula (XVI):

$R_{10}$, $R_{11}$, $R_{12}$ and $R_{13}$, which may be identical or different, represent aliphatic, alicyclic or arylaliphatic radicals containing from 1 to 6 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

A1 and B1 represent polymethylene groups containing from 2 to 8 carbon atoms, which may be linear or branched and saturated or unsaturated and may contain, bonded to or intercalated in the main chain, one or more aromatic rings, or one or more oxygen or sulfur atoms, or sulfoxide, sulfone, disulfide, amino, alkylamino, hydroxyl, quaternary ammonium, ureido, amide or ester groups, and $X^-$ denotes an anion derived from a mineral or organic acid;

A1, $R_{10}$ and $R_{12}$ can form, with the two nitrogen atoms to which they are attached, a piperazine ring; in addition, if A1 denotes a linear or branched, saturated or unsaturated alkylene or hydroxyalkylene radical, B1 can also denote a group —($CH_2$)n—CO-D-OC—($CH_2$)n— in which D denotes:

a) a glycol residue of formula: —O—Z—O, where Z denotes a linear or branched hydrocarbon-based radical or a group corresponding to one of the following formulae:

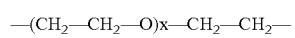

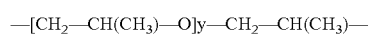

where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical

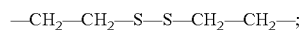

d) a ureylene group of formula: —NH—CO—NH—.

Preferably, $X^-$ is an anion, such as chloride or bromide.

These polymers have a number-average molecular weight generally between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that are formed from repeating units corresponding to formula (XVI) below:

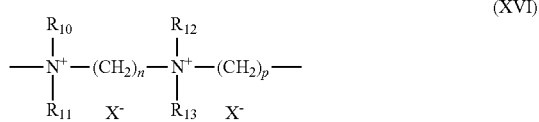

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 8 approximately, and $X^-$ is an anion derived from a mineral or organic acid. Mention may be made in particular of Mexomer PO sold by the company Chimex.

(11) Polyquaternary ammoniums formed from repeating units of formula (XVII):

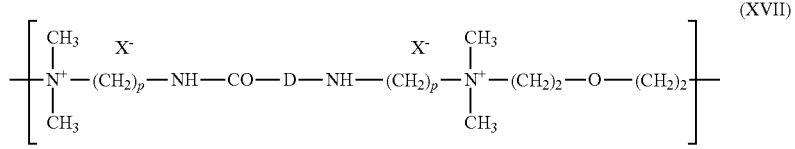

in which p denotes an integer ranging from 1 to 6 approximately, D may be nothing or may represent a group —$(CH_2)_r$—CO— in which r denotes a number equal to 4 or 7, and $X^-$ is an anion.

Such polymers may be prepared according to the processes described in U.S. Pat. Nos. 4,157,388, 4,702,906 and 4,719,282. They are especially described in patent application EP-A-122 324.

Among these polymers, examples that may be mentioned include the products Mirapol A 15, Mirapol AD1, Mirapol AZ1 and Mirapol 175 sold by the company Miranol.

(12) Quaternary polymers of vinylpyrrolidone and of vinylimidazole, for instance the products sold under the names Luviquat FC 905, FC 550 and FC 370 by the company BASF. These polymers may also comprise other monomers, for instance diallyldialkylammonium halides. Mention may be made in particular of the product sold under the name Luviquat Sensation by the company BASF.

(13) Polyamines such as Polyquart H sold by Henkel, which is given under the reference name Polyethylene Glycol (15) Tallow Polyamine in the CTFA dictionary, or oxyethylenated (15 OE) coconut polyamines.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers that may be used in the context of the present invention, it is preferred to use polymers of families (1), (2), (3), (4), (9), (10) and (12).

Preferably, the cationic polymer(s) are chosen from cationic celluloses, cationic guar gums and dimethyldiallylammonium halide homopolymers or copolymers.

More preferentially, the cationic polymer(s) are chosen from hydroxyalkylcelluloses, such as hydroxymethyl-, hydroxyethyl- or hydroxypropyl-celluloses grafted especially with a methacryloyl-ethyltrimethylammonium, methylacrylamidopropyl-trimethylammonium or dimethyldiallylammonium salt, cationic guar gums, and dimethyldiallylammonium chloride homopolymers or copolymers.

The additional cationic polymers other than the cationic acrylic copolymers as described previously may be present in an amount ranging from 0.01% to 15% by weight, preferably from 0.05% to 10% by weight and better still from 0.1% to 5% by weight relative to the total weight of the composition.

The cationic surfactant(s) that may be used in the composition according to the invention comprise, for example, optionally polyoxyalkylenated primary, secondary or tertiary fatty amine salts, quaternary ammonium salts, and mixtures thereof.

Examples of quaternary ammonium salts that may in particular be mentioned include:

those corresponding to the general formula (A4) below:

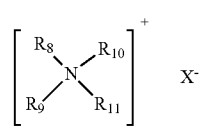

in which formula (A4):
$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and
$X^-$ represents an organic or mineral anionic counterion, such as that chosen from halides, acetates, phosphates, nitrates, $(C_1\text{-}C_4)$alkyl sulfates, $(C_1\text{-}C_4)$alkyl- and $(C_1\text{-}C_4)$alkylarylsulfonates, in particular methyl sulfate and ethyl sulfate.

The aliphatic groups of $R_8$ to $R_{11}$ may also comprise heteroatoms in particular such as oxygen, nitrogen, sulfur and halogens.

The aliphatic groups of $R_8$ to $R_{11}$ are chosen, for example, from $C_1\text{-}C_{30}$ alkyl, $C_1\text{-}C_{30}$ alkoxy, polyoxy$(C_2\text{-}C_6)$alkylene, $C_1\text{-}C_{30}$ alkylamide, $(C_{12}\text{-}C_{22})$alkylamido$(C_2\text{-}C_6)$alkyl, $(C_{12}\text{-}C_{22})$alkyl acetate, and $C_1\text{-}C_{30}$ hydroxyalkyl groups; $X^-$ is an anionic counterion chosen from halides, phosphates, acetates, lactates, $(C_1\text{-}C_4)$alkyl sulfates, and $(C_1\text{-}C_4)$alkylsulfonates and $(C_1\text{-}C_4)$alkylarylsulfonates.

Among the quaternary ammonium salts of formula (A4), preference is given firstly to tetraalkylammonium chlorides, for instance dialkyldimethylammonium or alkyltrimethylammonium chlorides in which the alkyl group contains approximately from to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A5) below:

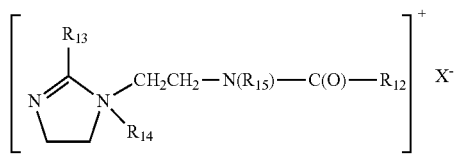

in which formula (A5):
$R_{12}$ represents an alkenyl or alkyl group comprising from 8 to 30 carbon atoms, for example fatty acid derivatives of tallow;
$R_{13}$ represents a hydrogen atom, a $C_1$-$C_4$ alkyl group or an alkenyl or alkyl group comprising from 8 to 30 carbon atoms;
$R_{14}$ represents a $C_1$-$C_4$ alkyl group;
$R_{15}$ represents a hydrogen atom or a $C_1$-$C_4$ alkyl group;
$X^-$ represents an organic or mineral anionic counterion, such as that chosen from halides, phosphates, acetates, lactates, ($C_1$-$C_4$)alkyl sulfates, ($C_1$-$C_4$)alkyl and ($C_1$-$C_4$)alkylaryl sulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;

quaternary diammonium or triammonium salts, particularly of formula (A6) below:

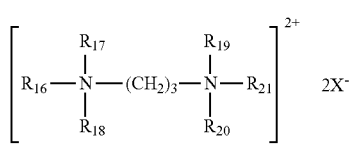

in which formula (A6):
$R_{16}$ denotes an alkyl group comprising approximately from 16 to 30 carbon atoms, which is optionally hydroxylated and/or interrupted with one or more oxygen atoms;
$R_{17}$ is chosen from hydrogen, an alkyl group comprising from 1 to 4 carbon atoms and a group $-(CH_2)_3-N(R_{16a})(R_{17a})(R_{18a})$, $X^-$;
$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and
$X^-$, which may be identical or different, represents an organic or mineral anionic counterion, such as that chosen from halides, acetates, phosphates, nitrates, alkyl($C_1$-$C_4$) sulfates, alkyl($C_1$-$C_4$)- and alkyl($C_1$-$C_4$) aryl-sulfonates, more particularly methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (A7) below:

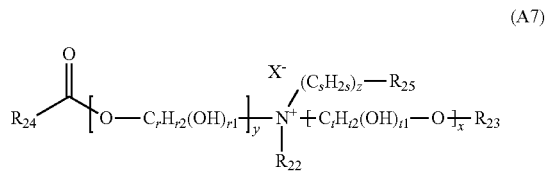

in which formula (A7):
$R_{22}$ is chosen from $C_1$-$C_6$ alkyl groups and $C_1$-$C_6$ hydroxyalkyl or $C_1$-$C_6$ dihydroxyalkyl groups;
$R_{23}$ is chosen from:
the group

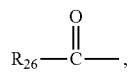

saturated or unsaturated, linear or branched $C_1$-$C_{22}$ hydrocarbon-based groups $R_{27}$,
a hydrogen atom,
$R_{25}$ is chosen from:
the group

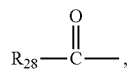

saturated or unsaturated, linear or branched $C_1$-$C_6$ hydrocarbon-based groups $R_{29}$,
a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6,
r1 and t1, which may be identical or different, are equal to 0 or 1, with r2+r1=2r and t1+t2=2t,
y is an integer ranging from 1 to 10,
x and z, which may be identical or different, are integers ranging from 0 to 10;
$X^-$ represents an organic or mineral anionic counterion, with the proviso that the sum x+y+z is from 1 to 15, that when x is 0 then $R_{23}$ denotes $R_{27}$, and that when z is 0 then $R_{25}$ denotes a linear or branched, saturated or unsaturated $C_1$-$C_6$ hydrocarbon-based radical $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, have the value 0 or 1.

Advantageously, y is equal to 1.

Preferably, r, s and t, which may be identical or different, have the value 2 or 3 and more particularly still are equal to 2.

The anionic counterion X⁻ is preferably a halide, such as chloride, bromide or iodide; a $(C_1$-$C_4)$alkyl sulfate or a $(C_1$-$C_4)$alkyl- or $(C_1$-$C_4)$alkylarylsulfonate. However, use may be made of methanesulfonate, phosphate, nitrate, tosylate, an anion derived from an organic acid, such as acetate or lactate, or any other anion which is compatible with the ammonium having an ester function.

The anionic counterion X⁻ is even more particularly chloride, methyl sulfate or ethyl sulfate.

Use is made more particularly, in the composition according to the invention, of the ammonium salts of formula (A7) in which:

$R_{22}$ denotes a methyl or ethyl group,
x and y are equal to 1,
z is equal to 0 or 1,
r, s and t are equal to 2,
$R_{23}$ is chosen from:
the group

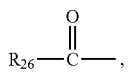

methyl, ethyl or $C_{14}$-$C_{22}$ hydrocarbon-based groups,
a hydrogen atom,
$R_{25}$ is chosen from:
the group

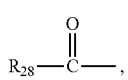

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based radicals are linear.

Among the compounds of formula (A7), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in patents U.S. Pat. No. 4,874,554 and 4,137,180.

Use may be made of behenoylhydroxypropyltrimethylammonium chloride sold by KAO under the name Quatarmin BTC 131.

Preferably, the ammonium salts comprising at least one ester function comprise two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

The cationic surfactants may be present in an amount ranging from 0.01% to 15% by weight, preferably from 0.05% to 10% by weight and better still from 0.1% to 5% by weight, relative to the total weight of the composition.

The content of conditioning agent in the composition according to the invention may range from 0.01% to 15% by weight relative to the total weight of the composition, preferably from 0.05% to 10% by weight and more preferentially from 0.1% to 5% by weight relative to the total weight of the composition.

Solvents

The composition comprises a cosmetically acceptable medium which generally comprises water, non-aqueous solvents, silicone solvents, and a mixture thereof.

More particularly, the organic solvents are chosen from linear or branched and preferably saturated monoalcohols and diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol, butylene glycol or dipropylene glycol monomethyl ether; and also diethylene glycol alkyl ethers, especially of $C_1$-$C_4$, for instance diethylene glycol monoethyl ether or monobutyl ether, alone or as a mixture.

More particularly, the silicone solvents are chosen from volatile and non-volatile silicones.

When they are volatile, the silicones are more particularly chosen from those with a boiling point of between 60° C. and 260° C., and even more particularly from:

(i) cyclic polydialkylsiloxanes containing from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the type such as dimethylsiloxane/methylalkylsiloxane, such as Silicone Volatile® FZ 3109 sold by the company Union Carbide, of formula:

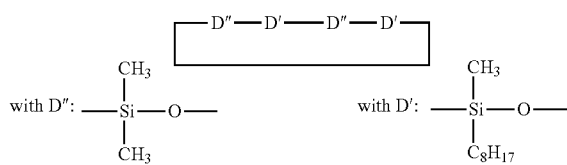

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, Jan. 76, pp. 27-32, Todd & Byers, "Volatile Silicone Fluids for Cosmetics".

Preferably, the water/ethanol mixture is preferred.

When they are present, the usual organic solvents described above usually represent from 1% to 95% by weight, more preferentially from 2% to 60% by weight, preferably from 3% to 55% by weight and better still from 8% to 50% by weight, relative to the total weight of the composition.

Thickeners

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas may be obtained by high-temperature hydrolysis of a volatile silicon compound in an oxyhydrogen flame, producing a finely divided silica. This process makes it possible in particular to obtain hydrophilic silicas bearing a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica via chemical reaction in order to reduce the number of silanol groups. It is especially possible to substitute silanol groups with hydrophobic groups: a hydrophobic silica is then obtained.

The hydrophobic groups may be:
trimethylsiloxyl groups, which are obtained in particular by treating fumed silica in the presence of hexamethyldisilazane. Silicas thus treated are known as Silica silylate according to the CTFA (6th Edition, 1995). They are sold, for example, under the references Aerosil R812® by Degussa and Cab-O-Sil TS-530® by Cabot.
dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener may represent from 0.1% to 30% by weight relative to the weight of the composition.

The composition may also comprise one or more organic thickeners.

These thickeners may be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulo se, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to one particular embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum or scleroglucan gum) and crosslinked acrylic acid or acrylamidopropanesulfonic acid homopolymers, and preferably from cellulose-based thickeners in particular with hydroxyethylcellulose.

The content of organic thickener(s), if they are present, usually ranges from 0.01% to 20% by weight and preferably from 0.1% to 5% by weight relative to the weight of the composition.

Surfactants

According to a particular embodiment of the invention, the composition also comprises one or more surfactants other than cationic surfactants.

In particular, the surfactant(s) are chosen from anionic, amphoteric, zwitterionic and nonionic surfactants, and preferentially nonionic surfactants.

The term "anionic surfactant" means a surfactant comprising, as ionic or ionizable groups, only anionic groups. These anionic groups are preferably chosen from the groups —C(O)OH, —C(O)O⁻, —SO₃H, —S(O)₂O, —OS(O)₂OH, —OS(O)₂O⁻, —P(O)O H₂, —P(O)₂O⁻, —P(O)₂O⁻, —P(OH)₂, =P(O)OH, —P(OH)O⁻, =P(O))O⁻, =POH and =PO⁻, the anionic parts comprising a cationic counterion such as those derived from an alkali metal, an alkaline-earth metal, an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglyco side polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates. When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine and triisopropanolamine salts, and 2-amino-2-methyl-1-propanol, 2-amino--methyl-1,3-propanediol and tris(hydroxymethyl)aminomethane salts.

Use is preferably made of alkali metal or alkaline-earth metal salts and in particular of sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

In particular, it is preferred to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

The amphoteric or zwitterionic surfactant(s), which are preferably non-silicone, which may be used in the present invention may in particular be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of ($C_8$-$C_{20}$)alkyl betaines, sulfobetaines, ($C_8$-$C_{20}$)alkylamido($C_3$-$C_8$)alkyl betaines and ($C_8$-$C_{20}$)alkylamido($C_6$-$C_8$)alkyl sulfobetaines.

Among the optionally quaternized secondary or tertiary aliphatic amine derivatives that may be used, as defined above, mention may also be made of the compounds of respective structures (A1) and (A2) below:

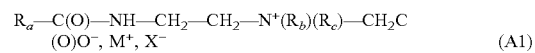

$R_a$—C(O)—NH—CH$_2$—CH$_2$—N$^+$(R$_b$)(R$_c$)—CH$_2$C(O)O⁻, M$^+$, X⁻ (A1)

in which formula (A1):
$R_a$ represents a $C_{10}$-$C_{30}$ alkyl or alkenyl group derived from an acid $R_a$COOH preferably present in hydrolyzed copra oil, or a heptyl, nonyl or undecyl group;
$R_b$ represents a β-hydroxyethyl group; and
$R_c$ represents a carboxymethyl group;
M$^+$ represents a cationic counterion derived from an alkali metal or alkaline-earth metal, such as sodium, an ammonium ion or an ion derived from an organic amine, and
X$^-$ represents an organic or mineral anionic counterion, such as that chosen from halides, acetates, phosphates, nitrates, ($C_1$-$C_4$)alkyl sulfates, ($C_1$-$C_4$)alkyl- and ($C_1$-$C_4$)alkylaryl sulfonates, in particular methyl sulfate and ethyl sulfate; or alternatively M$^+$ and X$^-$ are absent;

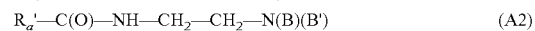

$R_a'$—C(O)—NH—CH$_2$—CH$_2$—N(B)(B') (A2)

in which formula (A2):
B represents the group —CH$_2$—CH$_2$—O—X;
B' represents the group —(CH$_2$)$_z$Y', with z=1 or 2;
X' represents the group —CH$_2$—C(O)OH, —CH$_2$—C(O)OZ', —CH$_2$—CH$_2$—C(O)OH or —CH$_2$—CH$_2$—C(O)OZ', or a hydrogen atom;
Y' represents the group —C(O)OH, —C(O)OZ', —CH$_2$—CH(OH)—SO$_3$H or the group —CH$_2$—CH(OH)—SO$_3$—Z;
Z' represents a cationic counterion derived from an alkali metal or alkaline-earth metal, such as sodium, an ammonium ion or an ion derived from an organic amine;
$R_a'$ represents a $C_{10}$-$C_{30}$ alkyl or alkenyl group derived from an acid $R_a$—C(O)OH, which is preferably present in coconut oil or in hydrolyzed linseed oil, an alkyl group, in particular a $C_{17}$ group and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of the compounds of formula (A3):

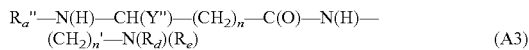  (A3)

in which formula (A3):
Y" represents the group —C(O)OH, —C(O)OZ", —CH$_2$—CH(OH)—SO$_3$H or the group —CH$_2$—CH(OH)—SO$_3$—Z";
R$_d$ and R$_e$, independently of each other, represent a C$_1$-C$_4$ alkyl or hydroxyalkyl group;
Z" represents a cationic counterion derived from an alkali metal or alkaline-earth metal, such as sodium, an ammonium ion or an ion derived from an organic amine;
R$_a$" represents a C$_{10}$-C$_{30}$ alkyl or alkenyl group derived from an acid R$_a$"—C(O)OH preferably present in coconut oil or in hydrolyzed linseed oil.
n and n' denote, independently of each other, an integer ranging from 1 to 3.

Among the compounds of formula (A3), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of (C$_8$-C$_{20}$)alkylbetaines such as cocoylbetaine, and (C$_8$-C$_{20}$)alkylamido(C$_3$-C$_8$)alkylbetaines such as cocamidopropylbetaine, and mixtures thereof. More preferentially, the amphoteric or zwitterionic surfactant(s) are chosen from cocamidopropylbetaine and cocoylbetaine.

Examples of nonionic surfactants that may be used in the composition used according to the invention are described, for example, in the "Handbook of Surfactants" by M. R. Porter, published by Blackie & Son (Glasgow and London), 1991, pp. 116-178.

Mention may be made, as examples of oxyalkylenated nonionic surfactants, of:
oxyalkylenated (C$_8$-C$_{24}$)alkylphenols;
saturated or unsaturated, linear or branched, oxyalkylenated C$_8$-C$_{30}$ alcohols;
saturated or unsaturated, linear or branched, oxyalkylenated C$_8$-C$_{30}$ amides;
esters of saturated or unsaturated, linear or branched, C$_8$-C$_{30}$ acids and of polyethylene glycols;
polyoxyethylenated esters of saturated or unsaturated, linear or branched, C$_8$-C$_{30}$ acids and of sorbitol;
esters of fatty acids and of sucrose;
(C$_8$-C$_{30}$)alkylpolyglycosides, (C$_8$-C$_{30}$)alkenylpolyglycosides, which are optionally oxyalkylenated (0 to 10 oxyalkylene units) and which comprise 1 to 15 glucose units, (C$_8$-C$_{30}$)alkylglucoside esters;
saturated or unsaturated oxyethylenated plant oils;
condensates of ethylene oxide and/or of propylene oxide, inter alia, alone or as mixtures;
N—(C$_8$-C$_{30}$)alkylglucamine derivatives and N—(C$_8$-C$_{30}$)acyl-methylglucamine derivatives;
aldobionamides;
amine oxides;
oxyethylenated and/or oxypropylenated silicones;
the surfactants containing a number of moles of ethylene oxide and/or of propylene oxide ranging advantageously from 1 to 100, more particularly from 2 to 100, preferably from 2 to 50 and more advantageously from 2 to 30. Advantageously, the nonionic surfactants do not comprise any oxypropylene units. In accordance with a preferred embodiment of the invention, the oxyalkylenated nonionic surfactants are chosen from oxyethylenated C$_8$-C$_{30}$ alcohols comprising from 1 to 100 mol and more particularly from 2 to 100 mol of ethylene oxide; polyoxyethylenated esters of saturated or unsaturated, linear or branched C$_8$-C$_{30}$ acids and of sorbitan comprising from 1 to 100 mol and better still from 2 to 100 mol of ethylene oxide. As examples of monoglycerolated or polyglycerolated nonionic surfactants, monoglycerolated or polyglycerolated C$_8$-C$_{40}$ alcohols are preferably used.

In particular, the monoglycerolated or polyglycerolated C$_8$-C$_{40}$ alcohols correspond to formula (A8) below:

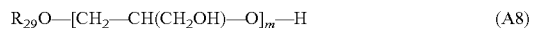  (A8)

in which formula (A8):
R$_{29}$ represents a linear or branched C$_8$-C$_{40}$ and preferably C$_8$-C$_{30}$ alkyl or alkenyl radical; and
m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the C$_8$/C$_{10}$ alcohol containing 1 mol of glycerol, the C$_{10}$/C$_{12}$ alcohol containing 1 mol of glycerol and the C$_{12}$ alcohol containing 1.5 mol of glycerol.

Preferably, the surfactant(s) are chosen from nonionic surfactants or from anionic surfactants. More particularly, the surfactant(s) present in the composition are chosen from nonionic surfactants.

Preferentially, the nonionic surfactant used in the composition according to the invention is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated, monoglycerolated or polyglycerolated surfactant and alkylpolyglucoside.

More preferably still, the nonionic surfactants are chosen from polyoxyethylenated sorbitol esters, polyoxyethylenated fatty alcohols and alkylpolyglucosides, and mixtures thereof.

The surfactants other than cationic surfactants may be present in the composition according to the invention in a content ranging from 0.1% to 50% by weight and better still from 0.5% to 20% by weight relative to the total weight of the composition.

Fatty Substances

The composition may comprise one or more fatty substances other than the functionalized silicones as described previously.

The term "fatty substance" means an organic compound that is insoluble in water at ordinary temperature (25° C.)

and at atmospheric pressure (760 mmHg or $1.013 \times 10^5$ Pa) (solubility of less than 5%, preferably of less than 1% and even more preferentially of less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain any salified carboxylic acid groups.

In addition, the fatty substances of the invention are not (poly)oxyalkylenated or (poly)glycerolated ethers.

The term "oil" means a "fatty substance" that is liquid at room temperature (25° C.) and at atmospheric pressure (760 mmHg or $1.013 \times 10^5$ Pa).

The term "non-silicone oil" means an oil not containing any silicon (Si) atoms and the term "silicone oil" means an oil containing at least one silicon atom.

More particularly, the fatty substance(s) are chosen from C6-C16 hydrocarbons, hydrocarbons containing more than 16 carbon atoms, non-silicone oils of animal origin, triglycerides of plant or synthetic origin, fluoro oils, fatty alcohols, esters of fatty acids and/or of fatty alcohols other than triglycerides and non-silicone waxes, in particular plant waxes, non-silicone waxes, and silicones other than the functionalized silicones, and mixtures thereof.

It is recalled that the fatty alcohols, esters and acids more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the C6-C16 hydrocarbons, they are more particularly linear or branched, and possibly cyclic, and are preferably alkanes. Examples that may be mentioned include hexane, cyclohexane, undecane, dodecane, tridecane or isoparaffins, such as isohexadecane, isodecane or isododecane, and mixtures thereof.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®, and mixtures thereof.

A hydrocarbon-based oil of animal origin that may be mentioned is perhydrosqualene.

The triglycerides of plant or synthetic origin are preferably chosen from liquid fatty acid triglycerides containing from 6 to 30 carbon atoms, for instance heptanoic or octanoic acid triglycerides, or alternatively, more particularly from those present in plant oils, for instance sunflower oil, corn oil, soybean oil, marrow oil, grapeseed oil, sesame oil, hazelnut oil, apricot oil, macadamia oil, arara oil, castor oil, avocado oil, jojoba oil, shea butter oil and synthetic caprylic/capric acid triglycerides, for instance those sold by the company Stéarineries Dubois or those sold under the names Miglyol® 810, 812 and 818 by the company Dynamit Nobel, and mixtures thereof.

Fluoro oils that may be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include cetyl alcohol, isostearyl alcohol, stearyl alcohol and a mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

As regards the esters of fatty acids and/or of fatty alcohols advantageously other than the triglycerides mentioned above and non-silicone waxes, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ and $C_1$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricino leate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate and cetyl octanoate, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar and fatty acid esters may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleate or dioleate, stearate, behenate, oleopalmitate, linoleate, linolenate or oleostearate.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% diester-triester-polyester;
the sucrose mono-dipalmito-stearate sold by the company Goldschmidt under the name Tegosoft® PSE.

The non-silicone wax(es) are chosen in particular from carnauba wax, candelilla wax, esparto wax, paraffin wax, ozokerite, plant waxes, such as olive tree wax, rice wax, hydrogenated jojoba wax and absolute flower waxes, such as the blackcurrant blossom essential wax sold by Bertin (France), and animal waxes, such as beeswaxes or modified beeswaxes (cerabellina); other waxes or waxy raw materials that may be used according to the invention are in particular marine waxes, such as that sold by Sophim under the reference M82, polyethylene waxes or polyolefin waxes in general.

The silicones that may be used in the composition of the present invention are volatile or non-volatile, cyclic, linear or branched silicones, having a viscosity from $5 \times 10^{-6}$ to 2.5 m$^2$/s at 25° C., and preferably $1 \times 10^{-5}$ to 1 m$^2$/s.

The silicones that may be used in accordance with the invention may be in the form of oils, waxes, resins or gums.

Preferably, the silicone(s) are chosen from polydialkylsiloxanes, especially polydimethylsiloxanes (PDMSs).

Use is preferably made of non-volatile polydialkylsiloxanes, polydialkylsiloxane gums and resins, and mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from Dow Corning, such as DC200, with a viscosity of 60 000 mm$^2$/s;
the Viscasil® oils from General Electric and certain oils of the SF series (SF 96, SF 18) from General Electric.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are especially polydialkylsiloxanes and preferably polydimethylsiloxanes with high number-average molecular weights of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;
mixtures of two PDMSs with different viscosities, and more particularly of a PDMS gum and of a PDMS oil, such as the product SF 1236 from General Electric. The product SF 1236 is a mixture of a gum SE 30 defined above, with a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

R2SiO2/2, R3SiO1/2, RSiO3/2 and SiO4/2 in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate-type resins sold in particular under the names X22-4914, X21-5034 and X21-5037 by the company Shin-Etsu.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Among these polyalkylarylsiloxanes, examples that may be mentioned include the products sold under the following names:

- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Preferably, the fatty substance(s) are non-silicone.

The fatty substance(s) are advantageously chosen from hydrocarbons containing more than 16 carbon atoms, C6-C16 alkanes, triglycerides or oils of plant origin, liquid synthetic triglycerides, fatty alcohols, esters of fatty acids and/or of fatty alcohols other than triglycerides and non-silicone waxes, or mixtures thereof. More preferentially, the fatty substance(s) are chosen from liquid petroleum jelly and liquid fatty alcohols such as 2-octyldodecanol and stearyl alcohol.

Additives

The composition according to the invention may also comprise one or more additives.

As additives that may be used in accordance with the invention, mention may be made of anionic, nonionic or amphoteric polymers or mixtures thereof, antidandruff agents, anti-seborrhoea agents, agents for preventing hair loss and/or for promoting hair regrowth, vitamins and pro-vitamins including panthenol, sunscreens, mineral or organic pigments, sequestrants, plasticizers, solubilizers, acidifying agents, opacifiers or nacreous agents, antioxidants, oxy acids, fragrances, preserving agents and ceramides.

Needless to say, those skilled in the art will take care to select this or these optional additional compounds such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

Preferably, in the composition according to the invention, the pH ranges from 3 to 11 and preferably from 4 to 9.

The composition according to the invention may be in the form of a wax, a paste, a cream, a foam, a spray (pump and aerosol) or a lotion. It may comprise one or more phases.

Process

The present invention also relates to a process for cosmetically treating keratin fibres, which consists in applying to said fibres an effective amount of a composition as described above.

The composition may be applied to wet or dry hair, preferably wet hair, with or without a leave-on time. In the case where a leave-on time is applied, it is between 2 minutes and 1 hour. The leave-on time may be carried out with heat, and in particular under an exclusive system of wrapper type.

The bath ratio of the formulation applied to the hair may be between 0.05 and 10, and more particularly between 0.05 and 5.

The product may be not rinsed out, or alternatively it may be rinsed out and/or shampooed (for less pronounced effects). The product is preferably not rinsed out.

The application may be followed by drying at room temperature and, optionally, by drying with a heating tool. One or more heating tools may be applied individually or successively to the hair at a temperature of between 40° C. and 250° C., preferentially between 90° C. and 250° C. and more preferentially between 100° C. and 210° C. for at time of between 2 seconds and 1 hour and preferentially between 2 seconds and 1 minute. The heating tool may be a straightening iron, a curling iron, a crimping iron, a waving iron, a hood, a hairdryer or an infrared heating system.

The heat application step may take place before, during or after the step of applying the composition, preferably during or after step of applying the composition. More preferentially, the heat application step takes place after the application of the composition. An optional leave-on time may take place between the application of the composition and the application of heat.

It has been observed that the composition affords very good working qualities, easy disentangling of wet and dry hair and a soft feel, without static electricity.

Multi-Application

The step of applying the composition according to one preferred embodiment as defined above may be implemented at least twice, preferably at least three times, more preferably at least five times.

Indeed, the repeated application of the composition according to the invention brings a very good effect in terms of fizz control.

It is also possible to apply the composition according to the invention, and then to apply heat. These two steps may be implemented twice, three times or more times. In particular, these two steps may be implemented five times.

Use

The present invention finally relates to the use of a composition as described above in the cosmetic treatment of keratin fibres and in particular hair.

The cosmetic treatment is preferably a care treatment.

The examples that follow serve to illustrate the invention without, however, being limiting in nature.

EXAMPLES

In the examples that follow, all the amounts are given, unless otherwise indicated, as mass percentages relative to the total weight of the composition (AM: active material).

Example 1

I. Compositions Tested

Examples of Compositions According to the Invention

Compositions A and B according to the invention and comparative compositions C and D were prepared using the ingredients whose contents are indicated in the table below as weight percentages.

|  | A | B | C (comp) | D (comp) |
|---|---|---|---|---|
| Copolymer 1 (containing 30% active material in ethanol) (1) | 16.7 | 16.7 | 16.7 | — |
| PEG-40/PPG-8 Methylaminopropyl/hydroxypropyl dimethicone copolymer at 30% in a glycerin/dipropylene glycol/water mixture (2) | 6.7 | — | — | 6.7 |
| Behenyltrimethylammonium chloride (79% AM, 18% isopropanol) (3) | — | 1 | — | — |
| Stearyl alcohol | — | 1.5 | — | — |
| Amodimethicone (58%), Trideceth-6 and cetrimonium chloride (4) | — | 1 | — | — |
| Dimethicone (50%), Laureth-23, Laureth-4 (5) | — | 5 | — | — |
| PPG-5-Ceteth-20 | — | 0.2 | — | — |
| Phenoxyethanol | — | 0.7 | — | — |
| Ethanol | 38.6 | 38.6 | 38.6 | 38.6 |
| Water | qs 100% | qs 100% | qs 100% | qs 100% |

(1) Plascize L-514
(2) Silsoft A+ from Momentive
(3) Genamine KPMD from Clariant
(4) Xiameter MEM-8299 from Dow Corning
(5) Xiameter MEM-2664

II. Application Protocols and Persistence Evaluation

The application protocol was as follows:
Shampooing
Application of the composition onto wet natural hair
Predrying with a hairdryer
Blow-drying with a hairdryer The evaluation protocol after drying relates to the impact on the shape, the cosmetic criteria (feel) and the appearance criteria (TEM visualization, macroscopic effects, static electricity).

The persistence evaluation protocol is as follows: Performance of several cycles:
Wetting of the hair
Shampooing
Rinsing
Drying with a hairdryer The evaluation relates to the impact on the shape, the cosmetic criteria (feel) and the appearance criteria of the locks.

III. Results

The sensorily evaluated locks of hair lead to the following observations:

COMPOSITION A: This coating sensorily gives the head of hair a mass, body and styling effect and also reinforcement at T0 and after shampooing. The shaping is facilitated. The split ends are rewelded together, for up to at least 5 shampoo washes. The working qualities of composition A are good, the product is easy to distribute, and brushing during the heat treatment presents no difficulties. The feel of the dry hair is good, and even after 1 and 5 shampoo washes the product is still perceptible on the fibre (good disentangling on wet and dry hair, good feel, individualized hairs, no tack during the heat treatments). There is no sign of static electricity.

COMPOSITION C: This coating sensorily gives the head of hair a mass, body and styling effect and also reinforcement at T0 and after shampooing. The split ends are rewelded together, for up to at least 5 shampoo washes. However, Copolymer 1 gives rise to a dragging, catching, tack sensation during brushing. Composition C distributes poorly over the head of hair. Dry hair after treatment has an acceptable feel, but this feel once again becomes poor when the hair is moistened and/or shampooed. Disentangling is very difficult. Separation of the individual hairs is observed, which is associated with repellent interactions of static electricity type.

COMPOSITION D: Good working qualities are observed, i.e. good distribution of the composition, easy blow-drying and easy brushing of the hair. After drying, the hair feels good. Moistened and/or shampooed hair is easy to disentangle. However, there is no shaping effect besides a manageability effect. After one shampoo wash, the hair regains its initial feel, and the effects afforded by composition D are no longer perceptible.

Example 2

I. Preparation of the Compositions

Compositions E1 and F1 according to the invention and comparative compositions E2, E3, F2 and F3 were prepared using the ingredients indicated in the tables below. The amounts are indicated in weight percentage of active material.

|  | E1 (inv) | E2 (comp) | E3 (comp) |
|---|---|---|---|
| Copolymer 1 (% am) (1) | 5 | 5 | — |
| Copolymer of vinylpyrrolidone and quaternized vinylimidazole (% am) (2) | 1 | — | 1 |
| Ethanol | qs 100% | qs 100% | qs 100% |

(1) Plascize L-514
(2) Polyquaternium-16

|  | F1 (inv) | F2 (comp) | F3 (comp) |
|---|---|---|---|
| Copolymer 1 (% am) (1) | 5 | 5 | — |
| Behentrimonium chloride (% am) | 1 | — | 1 |
| Ethanol | qs 100% | qs 100% | qs 100% |

(1) Plascize L-514

II. Application Protocol

Compositions E1, E2, E3, F1, F2 and F3 are applied on weakly sensitized locks of hair (alkaline solubility=20%, SA20), which have been beforehand washed. 0.15 g of composition per gram of locks is applied.

In order to evaluate the persistence of disentangling performance, locks of hair are then washed with a standard shampoo and rinsed.

III. Evaluation and Results

Performances in terms of persistence of disentangling criteria (wet hair) have been evaluated on a scale from 0 (very bad) to 5 (very good):

| Scale | Evaluation |
|---|---|
| 0 | Very bad |
| 0.5 | Very bad/Bad |
| 1 | Bad |
| 1.5 | Fairly bad/Bad |
| 2 | Fairly bad |
| 2.5 | Average |
| 3 | Fairly good |
| 3.5 | Good/Fairly good |
| 4 | Good |
| 4.5 | Very good/Good |
| 5 | Very good |

The expert grabs a comb into the locks of hair, from the root to the tip, and evaluates the easiness of passage.

Results are indicated in the tables below:

|  | E1 (inv) | E2 (comp) | E3 (comp) |
|---|---|---|---|
| After one shampoo | 3 | 1.5 | 2 |

|  | F1 (inv) | F2 (comp) | F3 (comp) |
|---|---|---|---|
| After one shampoo | 3 | 1.5 | 2 |

Locks of hair, which have been treated by compositions E1 or F1 according to the invention, have a better disentangling level after one shampoo than locks of hair which have been treated by compositions E2 and E3, or respectively F2 and F3.

As a consequence, the disentangling level after one shampoo has been improved in comparison with the prior art.

The invention claimed is:

1. A composition for styling hair comprising:
   (i) from 1% to 7% of a cationic acrylic copolymer comprising the following monomers:
      a) methacryloyloxyethyltrimethylammonium salt;
      b) butyl methacrylate; and
      c) ethoxyethyl methacrylate; and
   (ii) from 0.1% to 5% of behenyltrimethylammonium chloride,
   wherein all amounts are by weight, relative to the total weight of the composition.

2. The composition according to claim 1, wherein the total amount of the cationic acrylic copolymer is about 5% by weight, relative to the total weight of the composition.

3. The composition of claim 1, wherein the cationic acrylic copolymer has:
   monomer (a) in a proportion of 0.5% to 20%;
   monomer (b) in a proportion of 20% to 98%; and
   monomer (c) in a proportion of 1.5% to 95%, relative to the total number of monomer units.

4. The composition of claim 1, wherein the cationic acrylic copolymer has:
   monomer (a) in a proportion of 1% to 5%;
   monomer (b) in a proportion of 40% to 97%; and
   monomer (c) in a proportion of 2% to 55%, relative to the total number of monomer units.

5. The composition of claim 1, further comprising a functionalized silicone comprising a functional group chosen from amine groups, alkoxy groups, hydroxyl groups, or reactive groups.

6. The composition of claim 5, wherein the functionalized silicone is an amino silicone.

7. The composition of claim 1, further comprising a fatty substance chosen from C6-C16 hydrocarbons, non-silicone oils of animal origin, triglycerides of plant origin, triglycerides of synthetic origin, fluoro oils, fatty alcohols, esters of fatty acids, non-silicone waxes, or silicones other than functionalized silicones.

8. The composition of claim 1, further comprising a surfactant chosen from anionic surfactants, amphoteric surfactants, zwitterionic surfactants, nonionic surfactants, or mixtures thereof.

9. The composition of claim 1, further comprising from 0.5% to 20% of a surfactant chosen from anionic surfactants, amphoteric surfactants, zwitterionic surfactants, nonionic surfactants, or mixtures thereof.

10. The composition of claim 1, further comprising a mineral or organic thickening agent.

11. A composition for styling hair comprising:
    (i) from 1% to 7% of a cationic acrylic copolymer comprising the following monomers:
       a) methacryloyloxyethyltrimethylammonium salt;
       b) butyl methacrylate; and
       c) ethoxyethyl methacrylate;
    (ii) from 0.1% to 5% of behenyltrimethylammonium chloride;
    (iii) an amino silicone; and
    (iv) a surfactant chosen from anionic surfactants, amphoteric surfactants, zwitterionic surfactants, nonionic surfactants, or mixtures thereof,
    wherein all amounts are by weight, relative to the total weight of the composition.

12. A method for styling hair, comprising applying to the hair a composition comprising:
    (i) from 1% to 7% of a cationic acrylic copolymer comprising the following monomers:
       a) methacryloyloxyethyltrimethylammonium salt;
       b) butyl methacrylate; and
       c) ethoxyethyl methacrylate; and
    (ii) from 0.1% to 5% of behenyltrimethylammonium chloride,
    wherein all amounts are by weight, relative to the total weight of the composition.

13. The method according to claim 12, where the hair is heated before the step of applying the composition to the hair, during the step of applying the composition to the hair, or after the step of applying the composition to the hair.

14. The method according to claim 12, where the composition is applied to the hair at least two times.

15. The method according to claim 12, where the composition is applied to the hair at least three times.

16. The method according to claim 12, where the composition is applied to the hair at least four times.

17. The method according to claim 12, where the composition is applied to the hair at least five times.

* * * * *